(12) United States Patent
Draget et al.

(10) Patent No.: US 8,754,136 B2
(45) Date of Patent: Jun. 17, 2014

(54) GELATIN-CONTAINING TOPICAL COMPOSITION

(75) Inventors: Kurt Ingar Draget, Sandefjord (NO); Ingvild Johanne Haug, Sandefjord (NO); Olav Aasmund Smidsrod, Sandefjord (NO)

(73) Assignee: Aqua Bio Technology ASA, Sandefjord (NO)

( * ) Notice: Subject to any disclaimer, the term of this patent is extended or adjusted under 35 U.S.C. 154(b) by 1239 days.

(21) Appl. No.: 11/914,722

(22) PCT Filed: May 19, 2006

(86) PCT No.: PCT/GB2006/001874
§ 371 (c)(1),
(2), (4) Date: Aug. 27, 2008

(87) PCT Pub. No.: WO2006/123173
PCT Pub. Date: Nov. 23, 2006

(65) Prior Publication Data
US 2009/0131541 A1    May 21, 2009

(30) Foreign Application Priority Data

May 19, 2005  (GB) .................................. 0510286.8
Apr. 10, 2006  (GB) .................................. 0607174.0

(51) Int. Cl.
*A01N 25/00*    (2006.01)
*A61K 47/00*    (2006.01)
*A61K 9/00*     (2006.01)

(52) U.S. Cl.
USPC .......................................... 514/777; 424/400

(58) Field of Classification Search
USPC ......................................................... 514/777
See application file for complete search history.

(56) References Cited

U.S. PATENT DOCUMENTS

| | | | |
|---|---|---|---|
| 5,051,304 A | 9/1991 | David et al. | |
| 5,972,908 A | 10/1999 | Motte et al. | |
| 6,709,669 B1 * | 3/2004 | Murray et al. | 424/434 |
| 2004/0076666 A1 | 4/2004 | Green et al. | |

FOREIGN PATENT DOCUMENTS

| | | |
|---|---|---|
| CA | 1340242 | 12/1998 |
| DE | 3333444 A1 | 4/1985 |
| EP | 0347751 A1 | 12/1989 |
| EP | 1518552 A1 | 3/2005 |
| ES | 2039759 T3 | 10/1993 |
| JP | 01060335 A2 | 3/1989 |
| JP | H09-278639 | 10/1997 |
| JP | 2002-226356 | 8/2002 |
| JP | 2003-503316 | 1/2003 |
| JP | 2003-171256 | 6/2003 |
| JP | 2003231616 A2 | 8/2003 |
| JP | 2003-327599 | 11/2003 |
| KR | 2000026158 A | 5/2000 |
| KR | 2003004260 A | 1/2003 |
| MX | 2006PA132921 A | 1/2007 |
| RU | 2242969 C2 | 12/2004 |
| WO | WO 99/33924 | 7/1999 |
| WO | WO 00/10525 | 3/2000 |
| WO | WO 00/78857 A1 | 12/2000 |
| WO | WO 03/068008 A1 | 8/2003 |
| WO | WO 2005/120464 A1 | 12/2005 |

OTHER PUBLICATIONS

Huag, et al. (2004) "Physical Behaviour of Fish Gelatin-K-Carrageenan Mixtures." *Carbohydrate Polymers* 56:11-19.
Haug, I. et al. 2003 "Molecular interactions in, and rheological properties of, a mixed biopolymer system undergoing order/disorder transitions" *Food Hydrocolloids* 17:439-444.
Cosmetics Handbook 1996 by Nikko Chemicals Co., Ltd.; pp. 571-574.

* cited by examiner

*Primary Examiner* — Gina C Justice
*Assistant Examiner* — Michael B Pallay
(74) *Attorney, Agent, or Firm* — Knobbe, Martens, Olson & Bear, LLP

(57) ABSTRACT

This invention provides a topical pharmaceutical or cosmetic composition comprising a pharmaceutically or cosmetically active agent and a gelling agent, characterized in that said gelling agent comprises a fish gelatin and a polysaccharide.

12 Claims, 15 Drawing Sheets

GELATIN-CONTAINING TOPICAL COMPOSITION

RELATED APPLICATIONS

This application is a U.S. National Phase of International Application No. PCT/GB2006/001874, filed May 19, 2006, designating the U.S. and published in English on Nov. 23, 2006 as WO 2006/123173, which claims the benefit of British application No. 0510286.8, filed May 19, 2005, and British application No. 0607174.0, filed Apr. 10, 2006.

FIELD OF THE INVENTION

This invention relates to gelatin-containing topical compositions, e.g. pharmaceutical or cosmetic compositions for application to the skin, and to their preparation and use.

BACKGROUND OF THE INVENTION

Where a pharmaceutical or cosmetic composition is formulated for external topical application, it will generally also contain, in addition to the "active" component, components which will ensure the composition has appropriate properties for storage, application and skin-surface retention. In this regard, many such compositions currently contain mammalian gelatin, e.g. as a gelling agent.

Gelatin is a derivative of collagen, which is the most abundant protein in animals. Collagen is the major constituent of connective tissue, where it is present as water-insoluble collagen fibers. The general amino acid sequence is Gly-X-Y, where X often is proline and Y often is hydroxyproline. The content of the imino acids proline and hydroxyproline will differ from species to species, and collagen from homoiothermic animals (such as mammals) has a higher content of these imino acids compared to collagen from poikilothermic animals (such as fish).

Gelatin is most commonly produced from collagen from the bone and skin of cattle or pig by acid or alkali extraction procedures. These give, respectively, gelatin type A and type B which have different isoelectric points. The collagen molecule is a right-handed triple helix made up from three alpha-chains. The triple helices, the ordered conformation of collagen, are stabilised by proline and hydroxyproline units in the alpha-chains. The term collagen relates to the unmodified molecules found in the triple helices. Gelatin is the extracted collagen from which the terminal ends of the collagen molecules are lost. The gelling of gelatin is believed to be a result of regeneration of areas of triple helical structure (ordered conformation) interconnected by disordered amino acid segments (random coil). These gels are thermoreversible and both the gelling and melting temperatures are influenced by the content of proline and hydroxyproline. Gelatins from mammals, containing approximately 24% of these imino acids, have gelling and melting temperatures around 20-25° C. and 35-40° C., respectively. Cold water fish species contain only 16-18%, and fish gelatin typically gels below 8° C. and melts at 12-14° C. Hence, gels based on unmodified fish gelatin are only mechanically stable at temperatures corresponding to those found in refrigerators (0-5° C.).

Gelatins have been used for decades in pharmacology, foods and cosmetics as well as in photography, in glues and in composite materials. An increased search for alternatives to mammalian gelatin has been observed over the last decades, especially due to the outbreak of Bovine Spongiform Encephalopathy (BSE), a fatal neurological disorder of adult cattle which also may infect humans in the form of new variant Creutzfeldt—Jacob disease (nvCJD). Additionally, the use of mammalian gelatin is limited by religious concerns; neither Muslims (Halal/Haram), Jews (Kosher) nor Hindus accept gelatin from mammalian sources.

SUMMARY OF THE INVENTION

We have now found that the gelling properties of fish gelatins, which do not suffer from religious concerns regarding their use and which are free from risk of nvCJB, may be modified to produce compositions suitable for external topical application, e.g. to the skin, by coformulation with polysaccharide gelling agents. Thus for example such coformulation may produce compositions which have gelling characteristics equivalent or superior to those of compositions in which mammalian gelatin is used.

Thus viewed from one aspect the invention provides a topical pharmaceutical or cosmetic composition comprising a pharmaceutically or cosmetically active agent and a gelling agent, characterized in that said gelling agent comprises a fish gelatin and a polysaccharide.

The compositions of the invention may typically be in the form of gels, emulsions, creams, lotions, solutions, dispersions or the like and will typically contain further conventional ingredients such as solvents, colorants, aromas, stabilizers, pH modifiers, viscosity modifiers, skin penetration enhancers (e.g. DMSO), antioxidants, fillers, etc. They may contain further components such as encapsulation members, supports and the like, e.g. where they are to be applied as patches, for example for transdermal administration, for example by iontophoresis.

The compositions preferably contain a continuous aqueous phase having a gelling temperature in the range 10 to 30° C., more preferably 15 to 28° C. and a melting temperature in the range 20 to 42° C., more preferably 24 to 40° C., particularly 28 to 37° C.

In the case of the pharmaceutical compositions of the invention, the pharmaceutically active agent may be any drug substance capable of exerting a desired therapeutic or prophylactic effect at the site of application or following uptake through the skin, e.g. an antibiotic, antiinflammatory or antipruritic effect. Many if not most of the drug substances applied topically in conventional topical compositions (e.g. steroids, NSAIDs (for example ibuprofen), antifungals (for example ketoconazole), lithium compounds (for example for treating sebnorrhaic dermatitis or molluscum contagiosum), anti-acne compounds (for example azelaic acid), anti-dandruff agents (such as zinc pyrithione), etc.) may be used in the compositions of the invention. In the case of the cosmetic compositions of the invention, the cosmetically active agent may be any substance capable of exerting a desired cosmetic effect at the site of application or following uptake into the skin, e.g. vitamins, plant oils, UV absorbers, skin hydrating agents, cleansing agents, colorants, aromas, etc. Once again many if not most cosmetic agents applied topically in conventional topical compositions may be used in the compositions of the invention. Such active agents may be used in concentrations similar or comparable to the currently used concentrations.

The term polysaccharide as used herein refers to saccharide polymers with a backbone of carbohydrates that are capable of undergoing a sol/gel transition.

The polysaccharide gelling agents in the compositions according to the invention may come from a variety of sources, e.g. terrestrial or marine animals, plants, algae, etc. and they may be synthetic or naturally occurring polysaccharides or derivatives of naturally occurring polysaccharides.

Examples of suitable marine polysaccharides include carrageenans, alginates, agars and chitosans. Examples of suitable plant-derived polysaccharides include pectins. Examples of suitable microorganism-derived polysaccharides include gellans and scleroglucans. The use of charged, e.g. electrostatically charged and/or sulphated, polysaccharides is preferred as is the use of marine polysaccharides, in particular carrageenans and alginates, especially carrageenans. The invention is illustrated further below with particular reference to carrageenans.

The carrageenan family, which includes iota- and kappa-carrageenans, is a family of linear sulphated polysaccharides produced from red algae. The repeating disaccharide unit in kappa-carrageenan is β-D-galactose-4-sulphate and 3,6-anhydro-α-D-galactose, while that in iota-carrageenan is β-D-galactose-4-sulphate and 3,6-anhydro-α-D-galactose-2-sulphate. Both kappa- and iota-carrageenans are used in food preparations. The carrageenans are used as stabilisers, emulsifiers, gelling agents and fat replacers.

Both of these carrageenans form salt- or cold-setting reversible gels in an aqueous environment. Coil-helix transition and aggregation of helices form the gel network. Kappa-carrageenan has binding sites for specific monovalent cations, resulting in gel formation with decreasing shear and elastic moduli in the order $Cs^+>K^+>>Na^+>Li^+$. As a rule, an increasing salt concentration enhances the elastic modulus and the setting and melting temperatures of a kappa-carrageenan gel. The use of water-soluble potassium, rubidium, or cesium compounds, particularly potassium compounds, and particularly naturally occurring compounds (e.g. salts) is preferred when kappa-carrageenan is used according to the invention, e.g. at concentrations of up to 100 mM, more especially up to 50 mM. A salt-dependent conformational transition is also found for iota-carrageenan. The molecules are also known to undergo coil-helix transition with strong helix-stabilisation in the presence of multivalent cations, like $Ca^{2+}$. The use of water-soluble calcium, strontium, barium, iron or aluminium compounds, especially calcium compounds, and particularly naturally occurring compounds (e.g. salts) is preferred when iota-carrageenan is used according to the invention, e.g. at concentrations of up to 100 mM.

The polysaccharides used according to the invention will typically have weight average molecular weights of 5 kDa to 2 MDa, preferably 10 kDa to 1 MDa, most preferably 100 kDa to 900 kDa, particularly 400 to 800 kDa. The polysaccharides will typically be used at concentrations of 0.01 to 5% wt, preferably 0.1 to 1.5% wt., particularly 0.2 to 1% wt. Where mono or multivalent cations, typically group 1 or group 2 metal ions, are included in the compositions, this will typically be at concentrations in the range 2.5 to 100 mM, particularly 5 to 50 mM.

The fish gelatins used in the composition of the invention may be produced from the collagen of any aquatic species, however the use of gelatin from salt water fish and in particular cold water fish is preferred. Fish gelatins having an imino acid content of 5 to 25% wt. are preferred, more especially those having an imino acid content of 10 to 20% wt. The fish gelatin will typically have a weight average molecular weight in the range 10 to 250 kDa, preferably 75 to 175 kDa, especially 80 to 150 kDa. The fish gelatin will typically be present in the compositions at a concentration of 1 to 50% wt., preferably 2 to 15% wt., particularly 3 to 7% wt. Where an anti-ageing effect is desired, the fish gelatin used may optionally include a low molecular weight component, e.g. having a weight average molecular weight below 10 kDa. The weight ratio of fish gelatin to polysaccharide in the compositions of the invention will typically be 50:1 to 5:1, preferably 40:1 to 9:1, especially 20:1 to 10:1

The pH of the compositions of the invention is preferably in the range 3 to 9, more preferably 5 to 7.5.

The combination of fish gelatin and polysaccharides is synergistic resulting in compositions which form stable gels at ambient temperatures (at concentrations at which these components used individually do not) which have properties relevant to topical application which are unaccessible using the components individually or using conventional mammalian gelatins.

As mentioned above, fish gelatin from cold water species has considerably lower setting (<8° C.) and melting temperatures (below 14-15° C.) than mammalian gelatins. At room temperature (20-22° C.) the fish gelatin molecules are in a random coil conformation (unlike the mammalian gelatin molecules which are in the ordered conformation). Thus on its own fish gelatin is incapable of producing a gel composition which has mechanical stability at ambient temperatures. Nonetheless, the presence of the fish gelatin molecules in random coil conformation means that they exhibit improved water binding properties compared to molecules in ordered conformation. This is a major advantage for topical products as random coil conformation means that the fish gelatin can be optimally exploited as a skin moisture preserver. High molecular weight random coil fish gelatin will also be more efficient in retarding and absorbing water when present on the skin surface as a biopolymer film.

Mixing fish gelatin with polysaccharides it is possible to design gelling systems in which the fish gelatin still is present as random coil molecules, but where the system as a whole contributes to the mechanical properties of the skin product while still trapping water inside a hydrogel. The melting of such systems can be tailored towards specific temperatures by controlling by the mixing ratio of fish gelatin to polysaccharide. This allows a controlled meltdown of the combined gelatin/polysaccharide gel and the ability to form skin products with high water contents without further addition of artificial surfactants or fats/lipids.

The polysaccharide and fish gelatin combination thus forms an excellent moisture preserving film on the skin surface which sustains the hydration of the skin. Some of the random coil gelatin molecules may also penetrate the skin and replace some of the degraded collagen type I in the dermis. When it comes to penetration of molecules it is of great importance that the molecules are present as flexible random coils rather than as rigid and expanded ordered molecules like collagen and gelatin in the ordered conformation. Mammalian gelatins or collagens will never melt on the skin surface (28-32° C.) to give the optimum random coil conformation since these temperatures are significantly below the inner body temperature and hence also below the melting temperature of such gelatins and collagens.

A further advantage of the compositions of the invention is that the fish gelatin, which unlike mammalian gelatin is in random coil confirmation at skin temperatures, may penetrate into the skin to improve skin flexibility either by boosting skin collagen content or by providing an alternative substrate to the skin's own collagen for the endogenous matrix metalloproteinases which cause skin ageing.

Viewed from a further aspect the present invention provides a method of cosmetic treatment of a human subject comprising the application to the skin thereof of a cosmetic composition, characterised in that said composition is a composition according to the invention.

Viewed from a still further aspect the invention provides the use of fish gelatin and a polysaccharide gelling agent in the manufacture of a topically administrable drug substance-containing medicament for use in a method of treatment comprising application of said medicament to the skin of a human subject.

Viewed from a still further aspect the invention provides a method of treatment of a human subject comprising applying to the skin of said subject an effective amount of a pharmaceutical composition according to the invention.

Viewed from a yet still further aspect the invention provides a process for the manufacture of a composition according to the invention which process comprises admixing a fish gelatin, a polysaccharide gelling agent, a pharmaceutically or cosmetically active substance, and optionally and preferably water, said process optionally comprising emulsification of the admixture.

The uses, methods and processes of the invention may be effected using procedures conventional in the production and application of topical cosmetics and pharmaceuticals, in particular topical compositions containing mammalian gelatin.

The present invention enables the manufacture of optimised skin preparations with a high water content containing high molecular weight, or mixtures of high and low molecular weight fish gelatins, in random coil conformation, in mixture with one or several polysaccharides. This is achieved by tailoring the melting temperature of a combined fish gelatin/polysaccharide system towards the surface temperature of the skin. By using the invention, for the first time it is possible to control the melting behaviour of emulsified skin preparations by the aqueous phase rather than the lipid phase. The products give excellent moisture preserving film layers on the skin surface and thus sustain hydration of the skin. Penetration of random coil gelatin to the lower layers of the skin will improve the flexibility of the skin. These emulsified products will be stable as creams at room temperature due to their polysaccharide content. These optimised physical properties are valid both in the pure aqueous gel state as well as in emulsified systems in the presence of lipids, fats and oils. Such products can not be obtained with mammalian gelatins.

The following advantages in particular may be obtained using the present invention:

gels based on fish gelatin, and emulsions of such gels in the presence of lipids, may be produced which are mechanically stable at room temperature;

emulsified skin cream preparations which are room temperature stable and have a high water content may be produced;

the melting temperatures of such gels may be specifically tailored towards biological surfaces;

the rheological behaviour and texture of such gels may be optimized with respect to skin deposition;

cosmetic and pharmaceutical skin preparations may be made from bio-compatible polymers deriving from sustainable resources;

the user-friendliness of skin preparations may be improved, e.g. with respect to risk of disease and/or limitations based on religion;

skin preparations, based on mixtures of fish collagen and polysaccharides, may be produced which are readily soluble on biological surfaces;

skin preparations, based on mixtures of fish collagen and polysaccharides, may be produced which are optimized with respect to skin adsorption and stickiness; and an improved skin moisturising effect (due to applying gelatin in the disordered (random coil) state) may be achieved.

The fish gelatins penetrate into the skin and may thus be used to enhance skin penetration by other pharmaceutically or cosmetically active substances.

Thus viewed from a further aspect the invention provides a topical pharmaceutical or cosmetic composition comprising a pharmaceutically or cosmetically active agent and a skin penetration enhancing agent, characterized in that said skin penetration enhancing agent comprises a fish gelatin.

Viewed from a still further aspect the invention provides the use of a fish gelatin for the manufacture of a topical cosmetic or pharmaceutical composition containing a cosmetically or pharmaceutically active agent for use in a method of treatment comprising application of said medicament to the skin of a human or non-human mammalian subject.

The compositions containing a fish gelatin as a skin penetration enhancer will preferably also contain a polysaccharide such that a gelling effect is achieved. However the fish gelatin may be used other than as a component of a gelling agent and thus the compositions may take any format suitable for topical application, e.g. cream, paste, unguent, gel, emulsion, dispersion, suspension, solution, spray, etc. The use of solutions, creams, pastes and gels is particularly preferred. The active ingredient in the compositions may be any active agent it is desired to apply topically, e.g. as described earlier. The active ingredient however is especially preferably an analgesic, a substance suitable for combating a dermatological complaint (e.g. acne), a substance capable of combating radiation (e.g. sunshine) damage (e.g. glutathione), a blood flow stimulant (e.g. a vasodilator), etc.

Penetration of the fish gelatin into the skin also makes it available within the skin as an alternative substrate to the skin's own collagen for the endogenous matrix metalloproteinases which cause skin ageing.

Thus viewed from a further aspect the invention provides the use of a fish gelatin for the manufacture of a topical composition for application to the human skin to improve the flexibility thereof, e.g. by enhancing the collagen content thereof.

Viewed from a still further aspect the invention provides a method of treatment of a human subject to improve the flexibility of the skin thereof which method comprises applying to the skin of said subject an effective amount of a sterile, fish gelatin-containing composition, e.g. in the form of a cream, paste, unguent, wax, gel, emulsion, dispersion, suspension, solution or spray.

The compositions are desirably applied to the skin of at least one of the face, neck, upper arms, hands, upper chest, and lower thigh, in particular the face, neck and upper chest and especially around the eyes.

The fish gelatin used, and any polysaccharides used, in forming such compositions may be as described above.

The compositions used in accordance with the invention are preferably provided with instructions for their topical application, e.g. in package inserts, on container labels, or a container packaging. The compositions are desirably sterile and free of fish-tissue and moreover they preferably contain at least one pharmaceutical or cosmetic carrier or excipient.

BRIEF DESCRIPTION OF THE DRAWINGS

The compositions of the invention will now be illustrated further with reference to the following non-limiting Examples and to the accompanying drawings, in which.

DETAILED DESCRIPTION OF THE INVENTION

The following materials and methods were used throughout the Examples:

Carrageenans

Kappa-carrageenan (FMC Biopolymer A/S, Drammen, Norway) with an average molecular weight in the range of 400-800 kDa.

Iota-carrageenan (FMC Biopolymer A/S, Drammen, Norway) with an average molecular weight in the range of 400-800 kDa.

Fish Gelatin

Fish gelatin (FG) samples were produced from skins of cold-water fish species (Norland Inc., USA) with an average molecular weight in the range of 90-140 kDa.

Emulsification Model System

The model base was "Biodermica" day-cream (BIOlink AS, Sandefjord, Norway and Fitzone—KMB GmbH, Hamburg, Germany). The lipid and aqueous mixtures were prepared by emulsification with an ultra thurrax.

Ratios and percentages are by weight unless otherwise indicated.

EXAMPLE 1

Figure 1A:
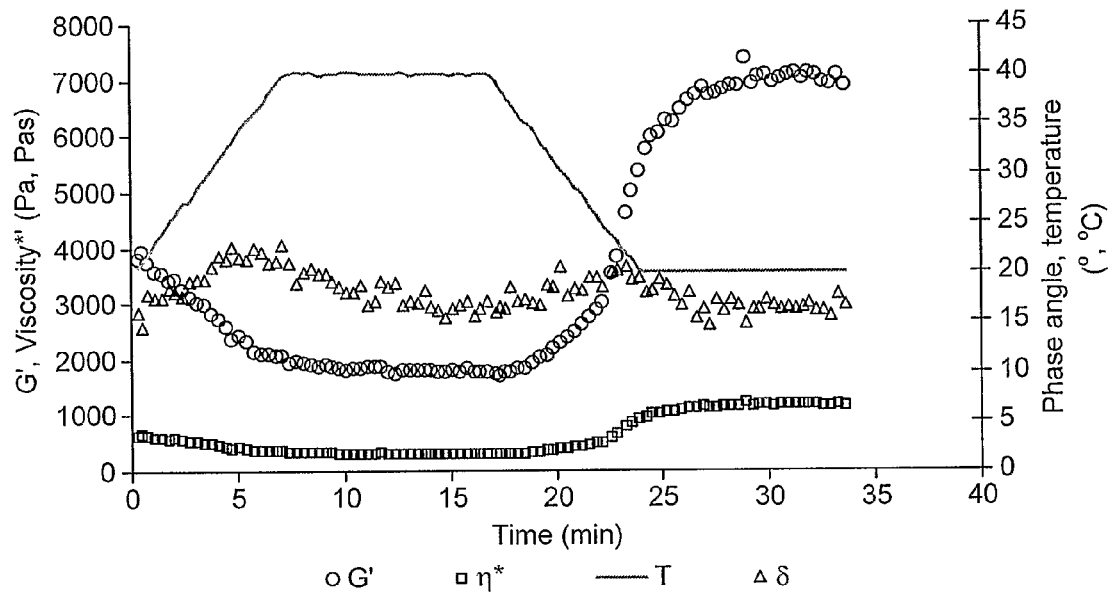
FIGS. 1a (melting and setting behaviour of base skin cream); 1b (melting and setting behaviour of base and water in the ratio 1:1); 1c (melting and setting behaviour of base and 10% (w/v) FG in the ratio 1:1); 1*d* (melting and setting behaviour of base in mixture with 0.75 (w/v) % CG+15 (w/v) % FG in the ratio 1:1); and 1*e* (melting and setting behaviour of base and 0.75% CG+15% FG+20 mM KCl mixed in the ratio 1:1) are plots of temperature (T), elastic modulus (G'), viscosity (η*) and phase angle (δ) against time for five compositions which are heated from 20 to 40° C. and cooled back to 20° C.

Overall Melting and Setting Behaviour of Base Skin Cream Emulsified with Blends (1:1) of Fish Gelatin and Kappa-Carrageenan, with Water and with a Pure Fish Gelatin Solution FIG. 1*a* shows the melting and restructuring of the pure base skin cream as the temperature is raised from 20 to 40° C. and reduced back to 20° C. The elastic modulus (G'), which reflects the solid properties of the cream, shows a slight temperature dependence with a monotonous slight decrease as the temperature is increased followed by a rather sharp increase as the temperature is lowered. This hysteresis is most probably due to the melting and re-crystallisation of the lipid components.

Figure 1B:
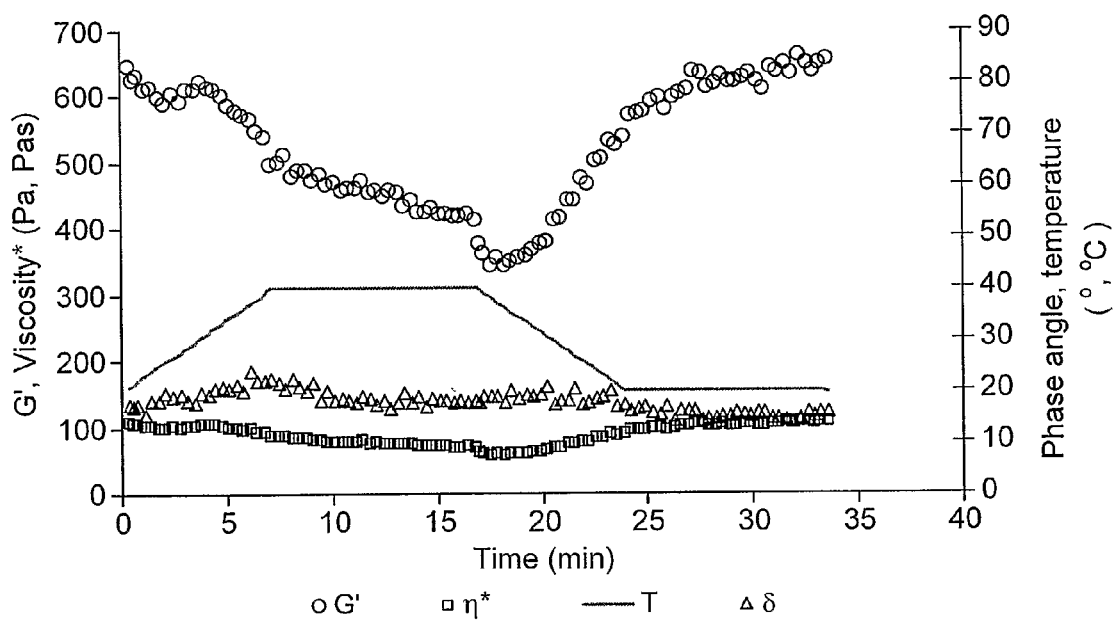

FIG. 1*b* shows the behaviour when base cream is mixed 1:1 with water. This mixture leads to an inhomogeneous product of a lotion type rather than a cream, hence showing non-desirable behaviour. This is due to the suboptimal effect of the water in the system leading to a lack of stability. A grainy consistency due to larger water domains (suggesting full phase separation with time) was also observed in this product.

Figure 1C:
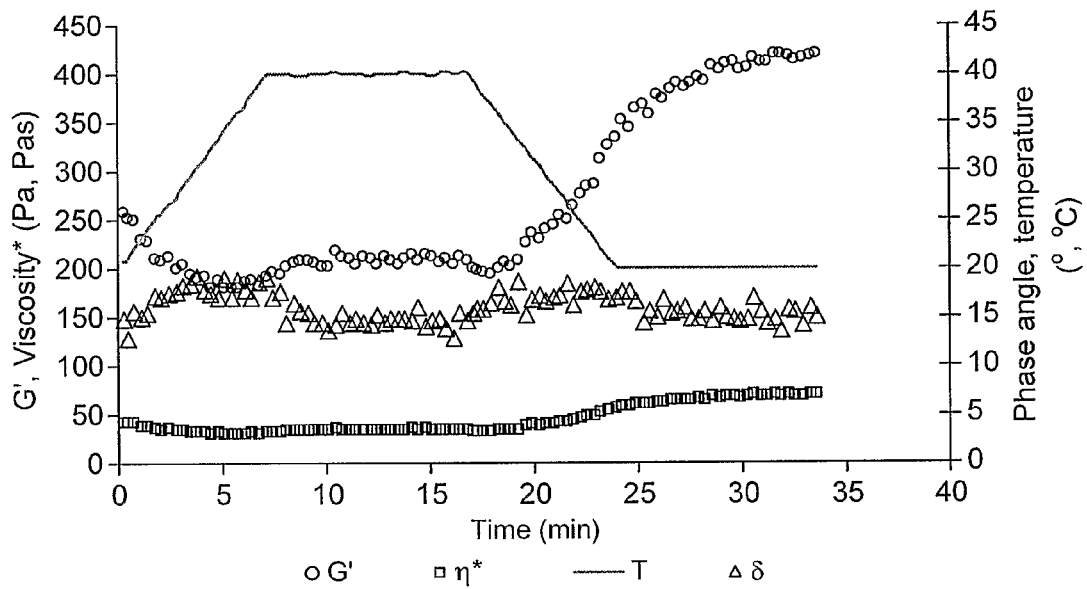

FIG. 1*c* shows the behaviour when base cream is mixed 1:1 with a 10% fish gelatin aqueous solution. In this example, the hysteresis behaviour of the pure cream (see FIG. 1*a*) is also seen. G', however, is very low, implying poor mechanical properties.

Figure 1D:
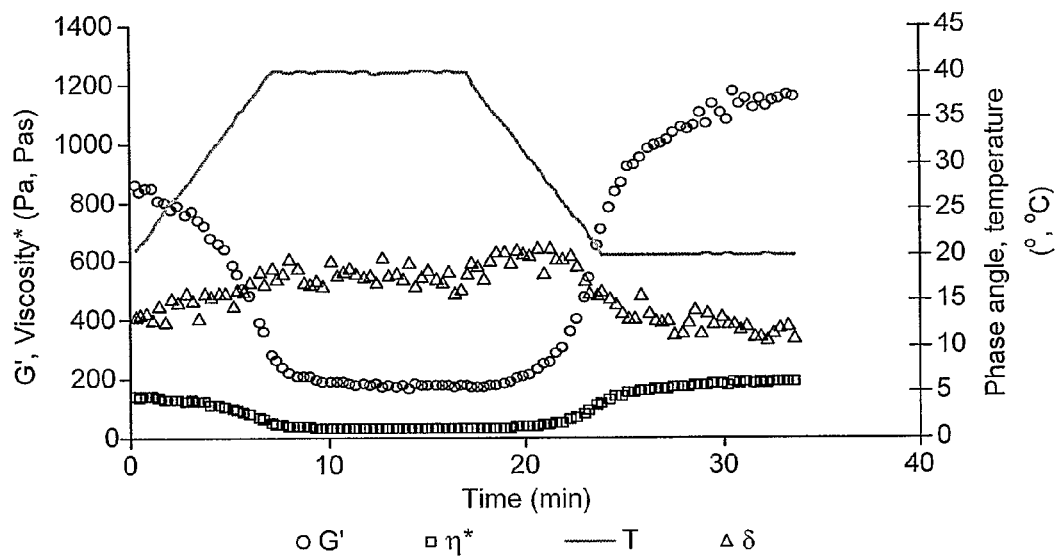

FIG. 1*d* shows the behaviour when base cream is mixed 1:1 with an aqueous solution containing 0.75% kappa carrageenan and 15% fish gelatin. This gel is tailored to melt on the human skin. A very pronounced effect is seen when the temperature is raised, and the hysteresis seen in FIG. 1*a* is again seen when the temperature is lowered. A smooth, soothing product was obtained.

Figure 1E:
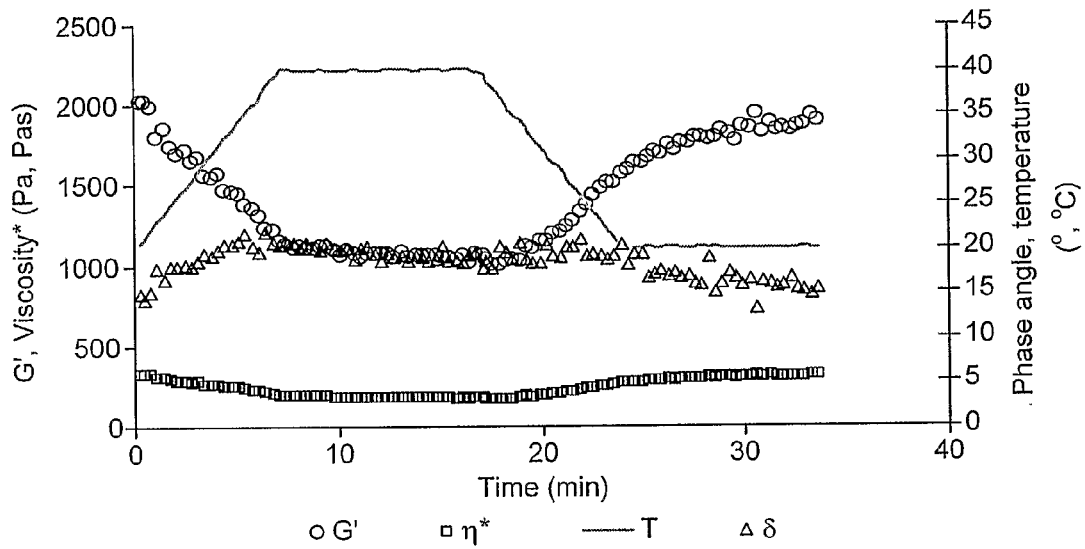

FIG. 1*e* shows the behaviour when base cream is mixed 1:1 with a solution of 0.75% kappa-carrageenan and 15% fish gelatin and with 20 mM KCl. This mixture is designed to keep its mechanical structure also on the skin surface. A picture now emerges that resembles that of the pure base cream (FIG. 1*a*) except for the hysteresis after cooling of the system. This result suggests that the mechanical properties in this non-melting product are considerably more governed by the polysaccharide content.

EXAMPLE 2

Figure 2A:
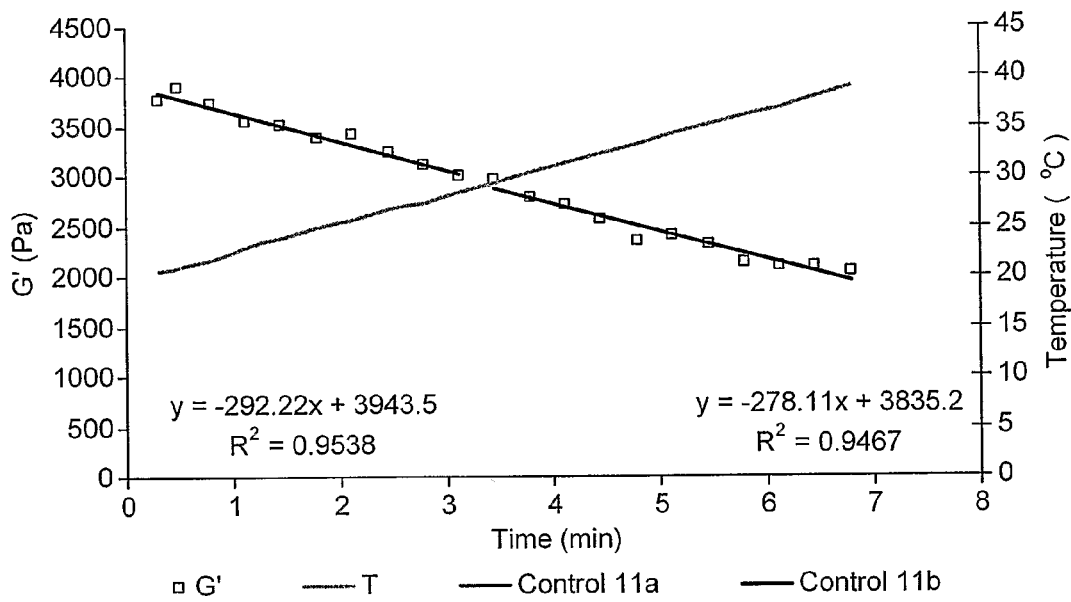
FIGS. 2*a* (melting-out of pure base skin cream); 2*b* (melting-out of a blend of base and water in the ratio 1:1); 2*c* (melting-out of a mixture of base and 10% FG in the ratio 1:1); 2*d* (melting-out of a mixture of base and 0.75% CG+15% FG in the ratio 1:1); and 2*e* (melting-out of a mixture of base and 0.75 (w/v) % CG+15 (w/v) % FG+20 mM KCl in the ratio 1:1) are plots of temperature (T) and elastic modulus (G') against time for five compositions as they are heated from 20 to 40° C.
Figure 2B:
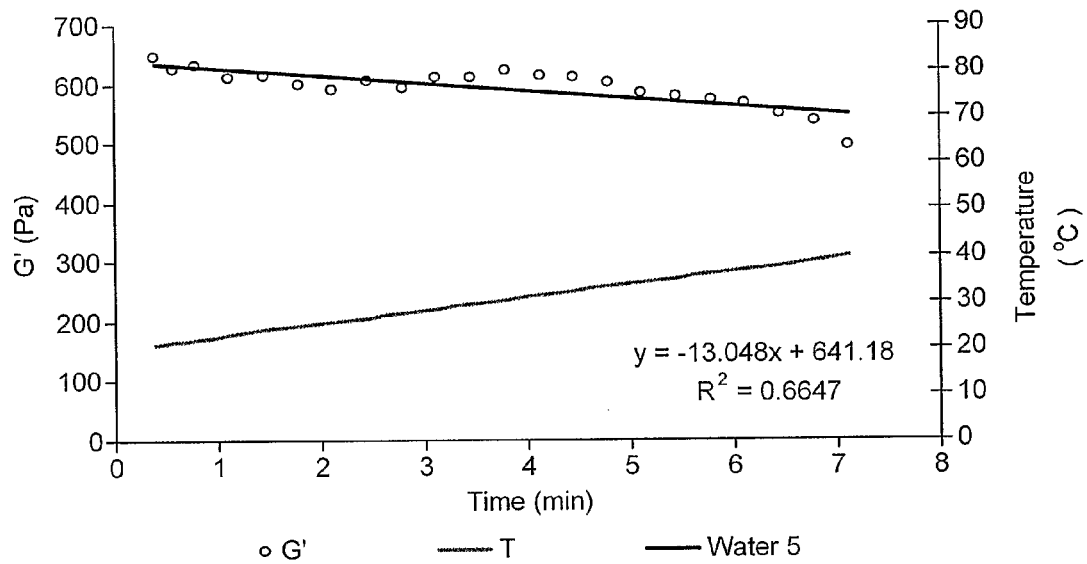
Figure 2C:
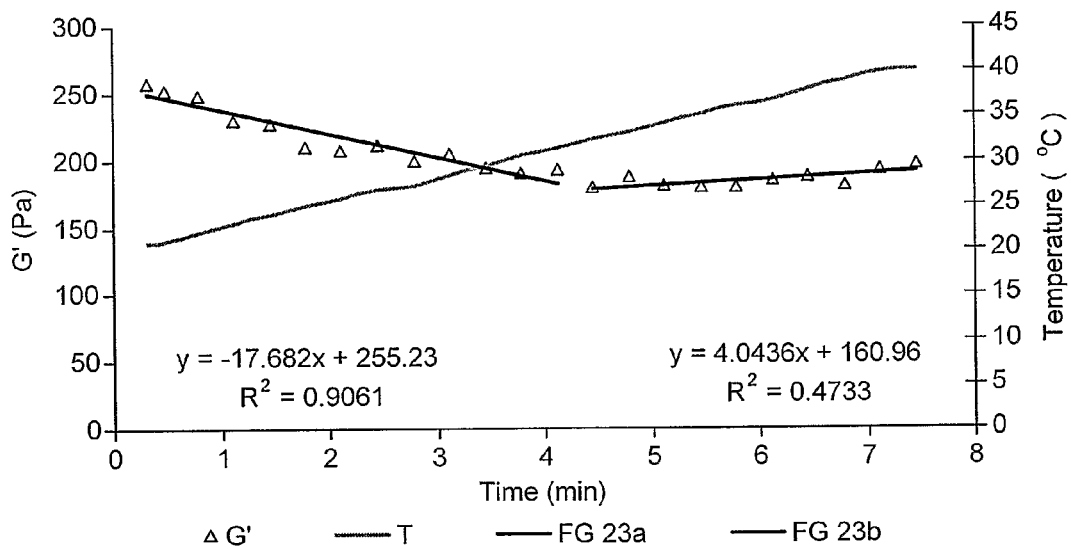
Figure 2D:
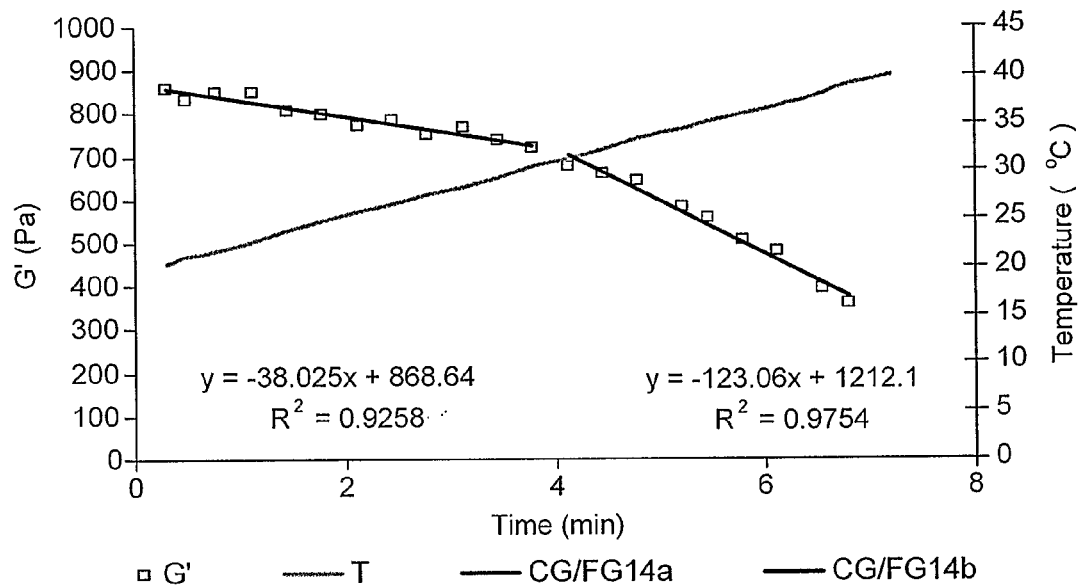
Figure 2E:
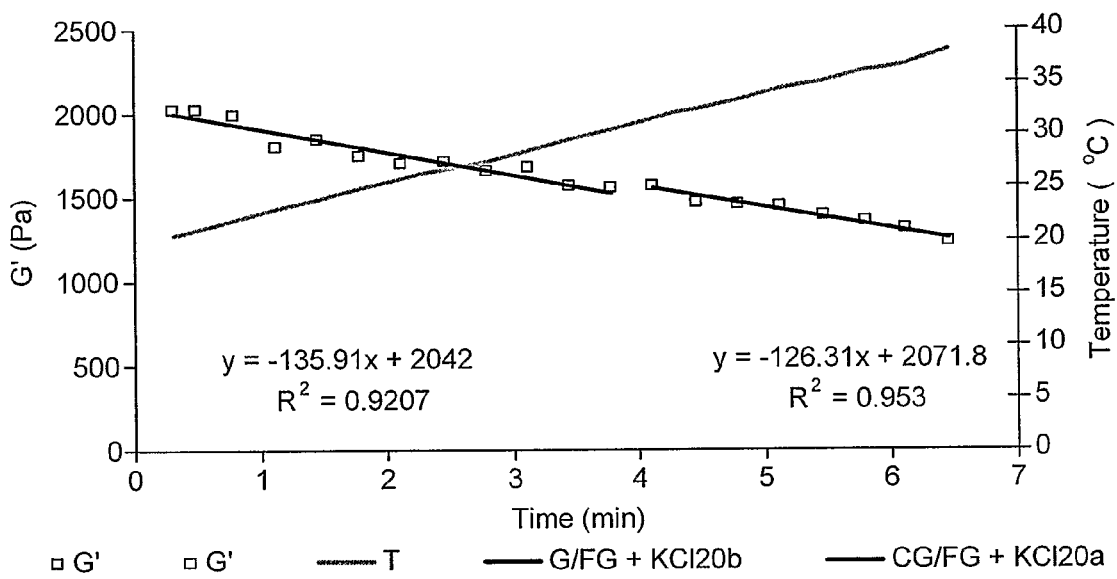

Initial Melting Behaviour of Base Skin Cream Emulsified with Blends (1:1) of Fish Gelatin and Kappa-Carrageenan, with Water and with a Pure Fish Gelatin Solution. Skin Contact Behaviour FIGS. 2a-2e correspond to the initial phase of FIGS. 1a-1e. It is clearly seen that the sample tailored to melt on human skin (FIG. 2d) is the only sample showing a pronounced break in the development of G' around skin temperature (30° C.) indicating that the fish gelatin/carrageenan gel melts and thus facilitates the distribution of the random coil gelatin on the skin. All other samples show a more or less monotonous decrease in G' with decreasing temperature indicating that the weakening of the cream is due to changes in the lipid phase.

EXAMPLE 3

Stress Tolerance of Base Skin Cream Emulsified with Blends (1:1) of Fish Gelatin and Kappa-Carrageenan, with Water and with a Pure Fish Gelatin Solution. Stability at 20° C.

Figure 3A:
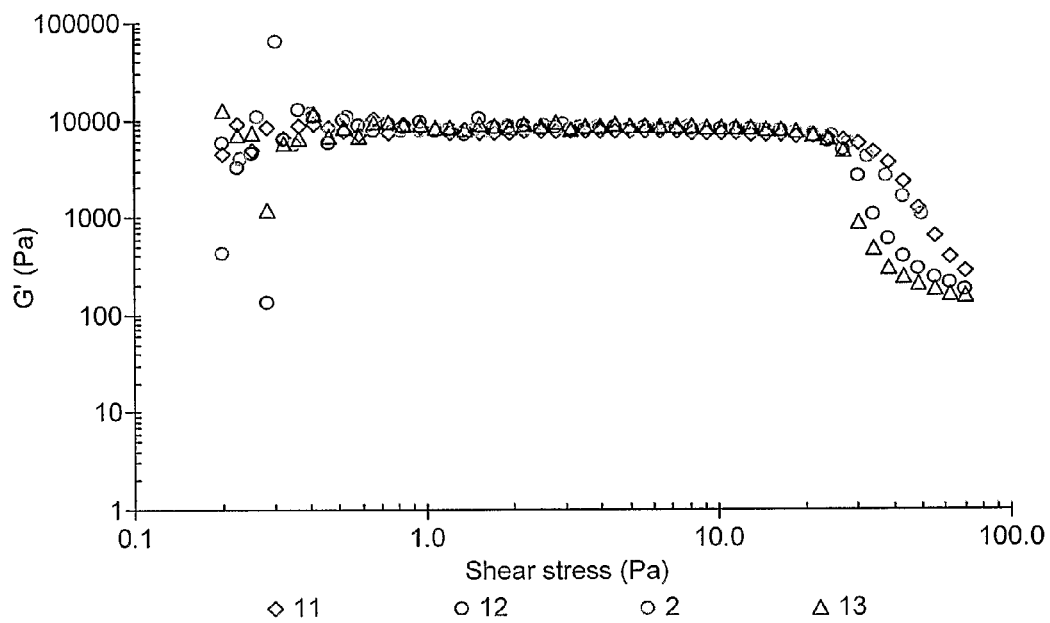
FIGS. 3*a* (mechanical response of pure base skin cream at increasing shear stress. Several replicates), 3*c* (mechanical response of base:water 1:1 with increasing shear stress. Several replicates), 3*e* (mechanical response in a mixed system of base: 10% FG (1:1) with increasing shear stress. Several replicates), 3*g* (mechanical response in mixed systems of base:FG/CG/water (1:1) with increasing sheer stress. Several replicates. 2=0.5% CG+10% FG, 14–16=0.75% CG+15% FG) and 3*i* (mechanical response in mixed systems of base: FG/CG/20 mM KCl/water (1:1) with increasing shear stress. Several replicates) are plots of elastic modulus (G') against shear stress and FIGS. 3*b* (change in phase angle for pure base with increasing shear stress), 3*d* (change in phase angle for a mixed system of base:water (1:1) with increasing shear stress), 3*f* (change in phase angle for a mixed system of base: 10% FG (1:1) with increasing shear stress), 3*h* (change in phase angle for systems of base:FG/CG/water (1:1) with increasing shear stress. No flow at high shear stresses. 2=0.5% CG+10% FG, 14–16=0.75% CG+15% FG) and 3*j* (change in phase angle for systems of base:FG/CG/20 mM KCl/water (1:1) with increasing shear stress. No flow at high shear stresses) are plots of phase angle (δ) against shear stress for five compositions each of which is subjected to increasing shear stress several times over (the run numbers appear beneath the plots)
Figure 3B:
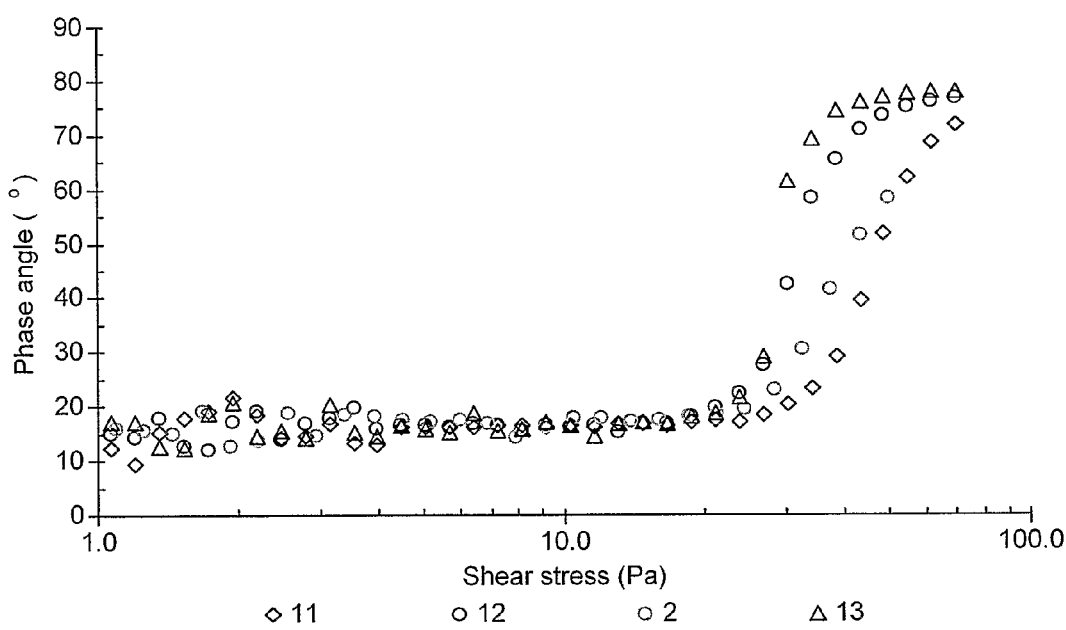

FIGS. 3a and 3b show the mechanical response (development of G' and the phase angle $\delta$) of the pure base skin cream. It is seen that the cream starts to flow (G' decreases and $\delta$ increases) at a stress around 20 Pa. There is also a nice reversibility of the system in the sense that no change is observed in the linear region or in the onset of flow when the cream is tested several times.

Figure 3C:
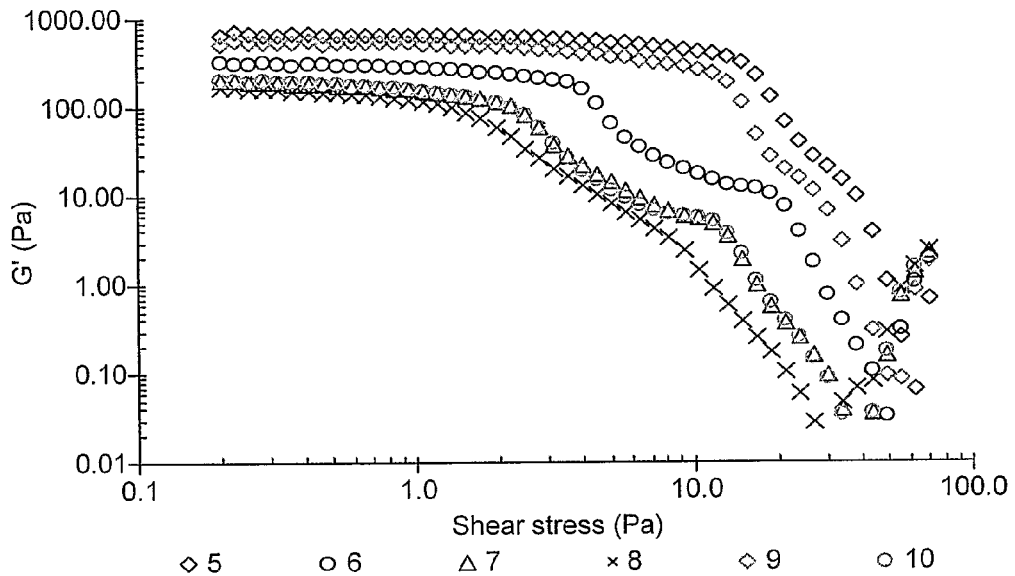
Figure 3D:
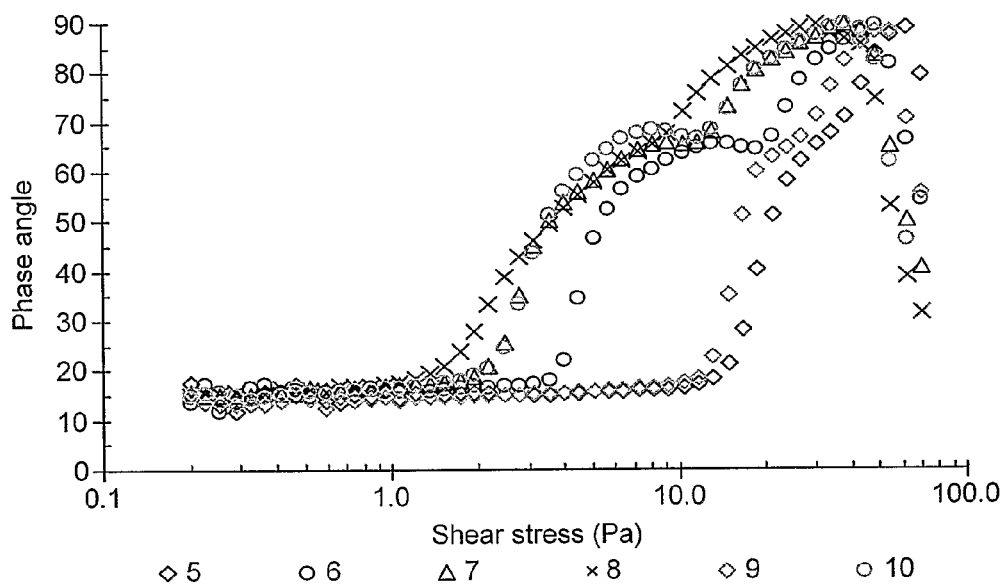

FIGS. 3c and 3d show the same response in a 1:1 blend of base and water. It is clearly seen that the system starts to flow at a considerable lower stress, and that the stress necessary to induce flow becomes smaller with repeated stress cycles suggesting a non-equilibrium system and a sub-optimal product.

Figure 3E:
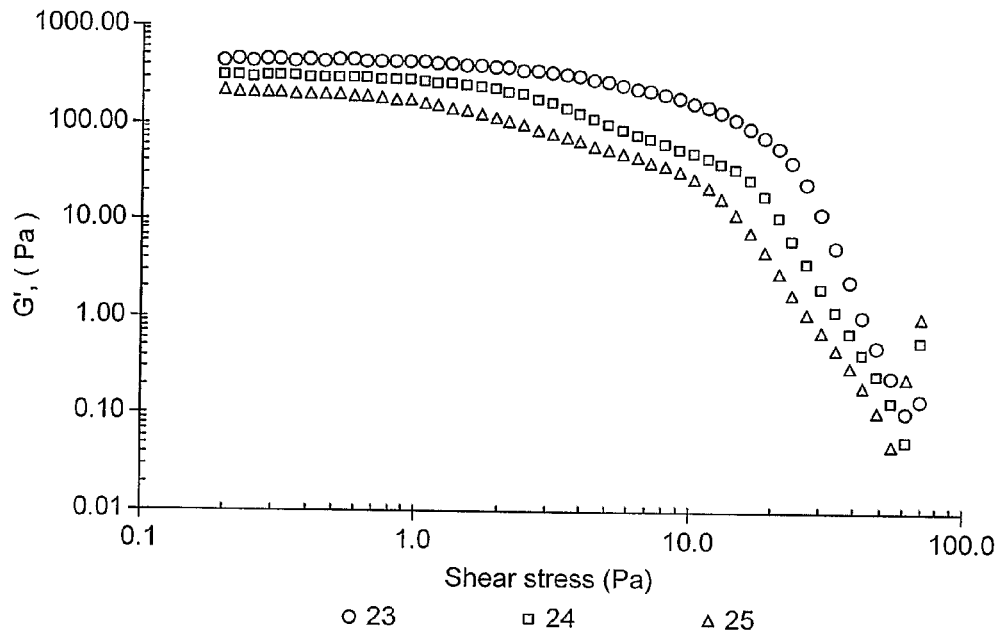
Figure 3F:
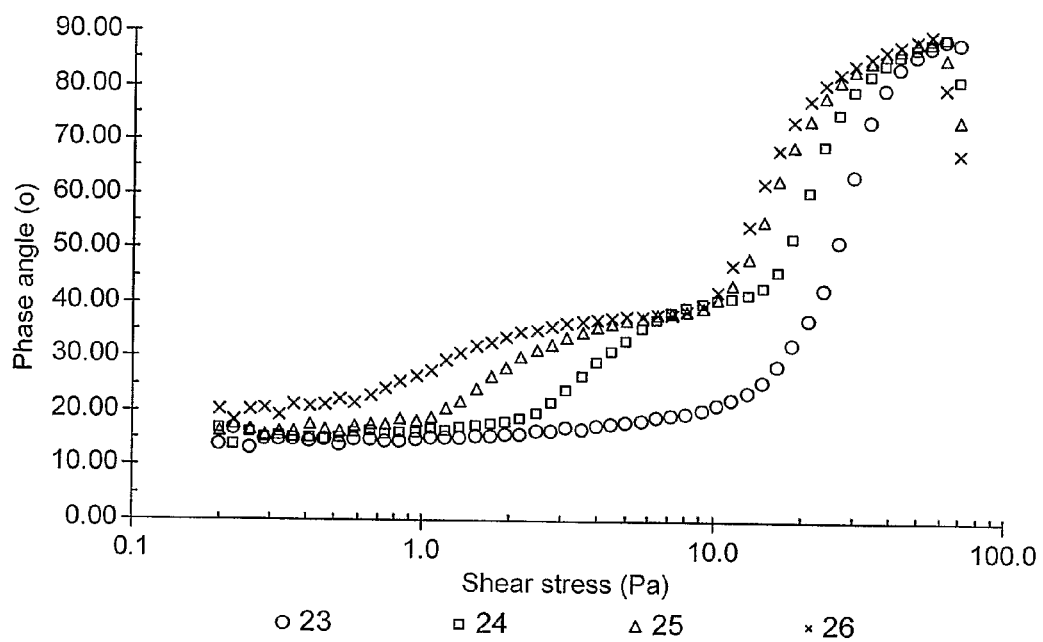

FIGS. 3e and 3f show the stress behaviour of a 1:1 blend of base and a 10% aqueous solution of fish gelatin. As in the case of the water blend, this system also exhibits a flow at considerably lower stresses and a dependency of the flow inducing stress with respect to the number of deformation cycles. This shows that fish gelatin alone is not sufficient to give a stable skin cream.

Figure 3G:
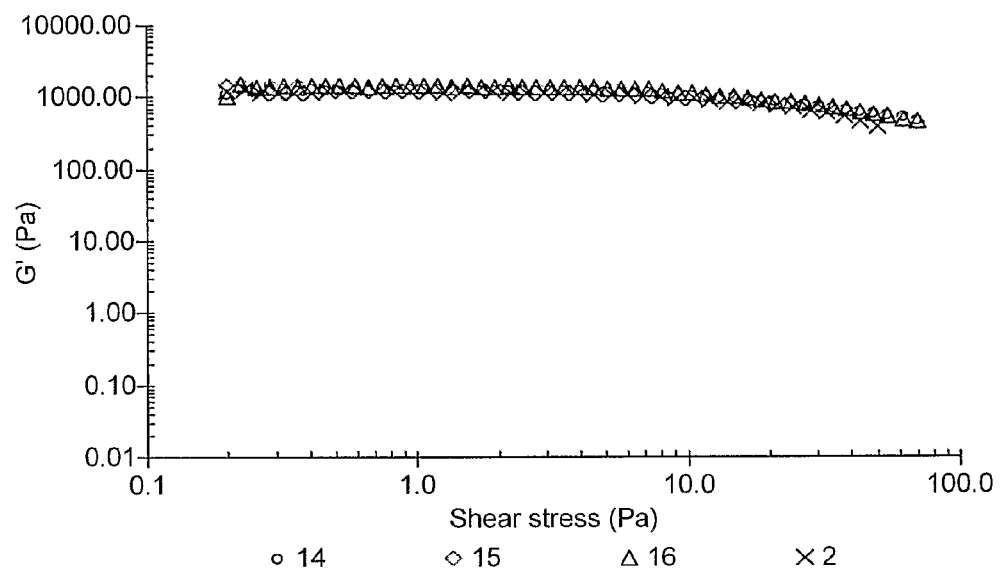
Figure 3H:
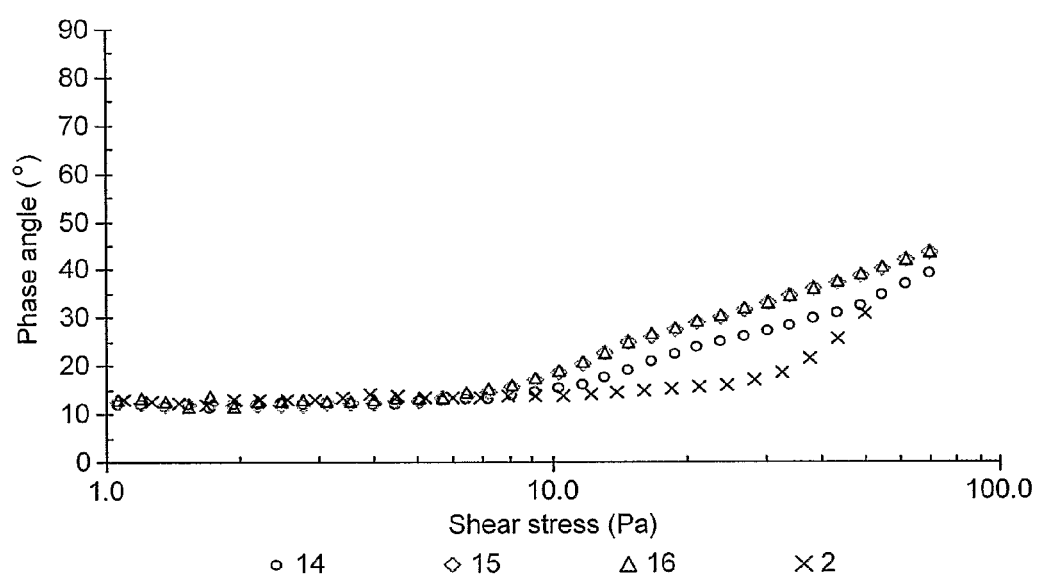

FIGS. 3g and 3h show the stress induced mechanical response of the 1:1 mixture of base skin cream and two aqueous mixtures of fish gelatin and kappa-carrageenan (15%/0.75% and 10%/0.50%). These systems prove to be very different from the addition of pure water and 10% fish gelatin due to the fact that they do not flow until stresses which are comparable to those needed for the pure base cream, and they are also fully reversible systems (i.e. the mechanical response does not depend on the number of deformation cycles). Furthermore, looking at the phase angle, shows that these gels do not become liquid-dominant at all within the stress regime tested (phase angle, $\delta$, is always lower than 45°). This reflects the importance of the gelled polysaccharide in the stabilisation of the cream. Hence, this 1:1 mixture with increased water content is a more stable product than the pure base cream at 20° C.

Figure 3I:
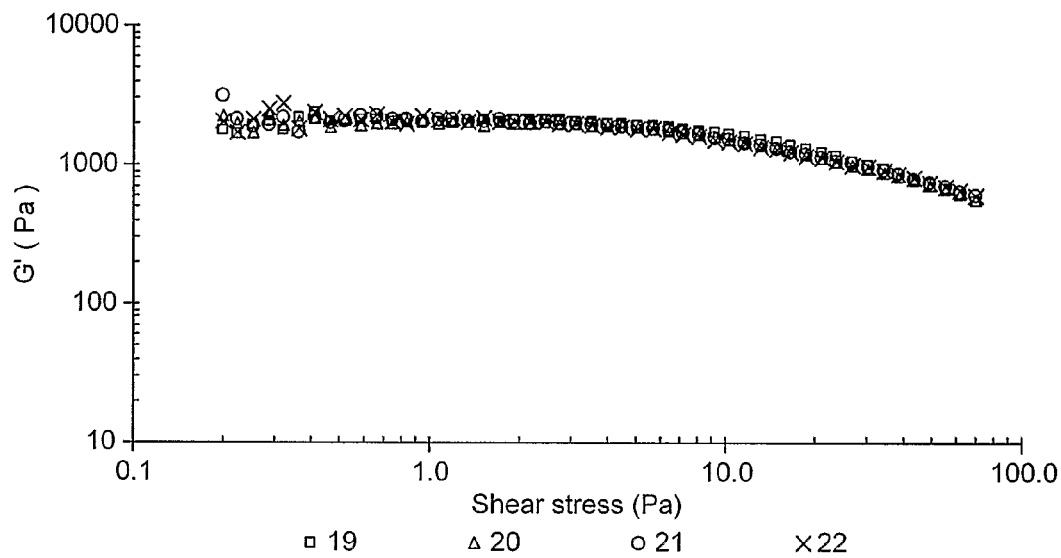
Figure 3J:
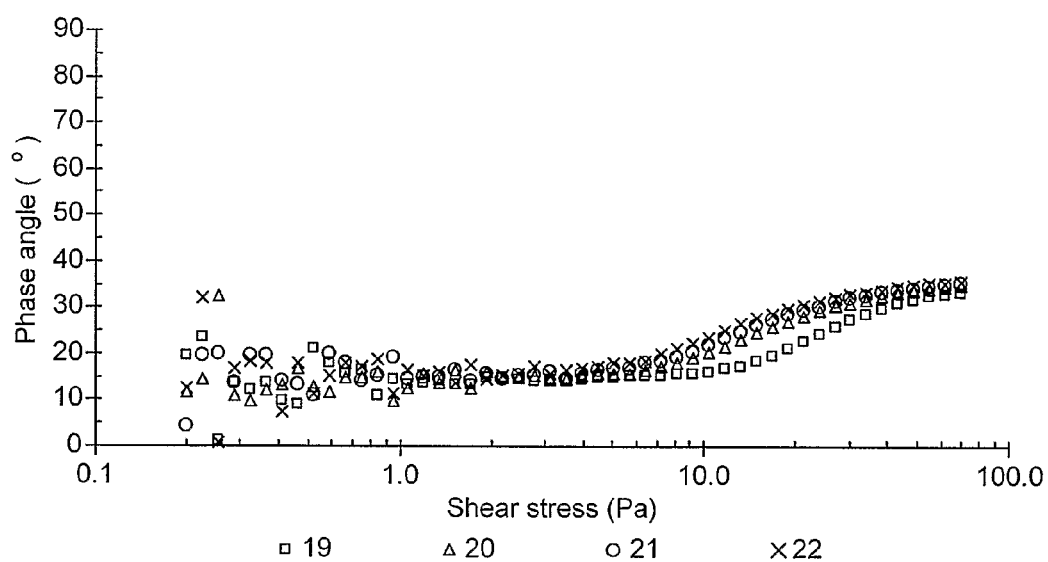

FIGS. 3i and 3j show the mechanical response of the 1:1 mixture of base and the fish gelatin/kappa-carrageenan blend with a 20 mM addition of the gel promoting ion K+. These figures show that it is possible to make the system even more stable by the addition of such ions due to the extra stabilisation of the carrageenan network. In this system, the phase angles, are still lower at the highest stress tested compared to the non-flowing mixed system without any extra potassium ions.

EXAMPLE 4

Figure 4A:
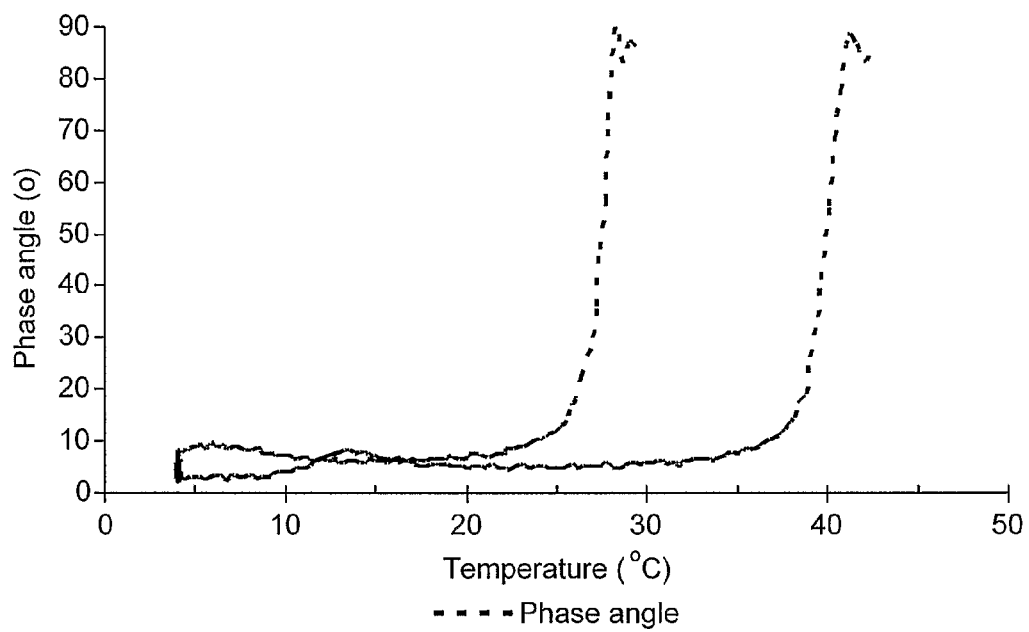
FIG. 4*a* (changes in phase angle with temperature for a mixed 0.5 (w/v) % κ-CG and 10 (w/v) % FG aqueous system. Gelling occurs at 27° C. and melting at 40° C.), 4*b* (small-strain oscillatory measurements of 0.5 (w/v) % κ-CG. Changes in phase angle with temperature. Gelling occurs at 13° C. and melting at 29° C.), 4*c* (small-strain oscillatory measurements of 10 (w/v) % FG. Changes in phase angle with temperature. Gelling occurs at 4° C. and melting at 13° C.), are plots of phase angle (δ) against temperature for three compositions which are melted and then cooled to form gels.
Figure 4B:
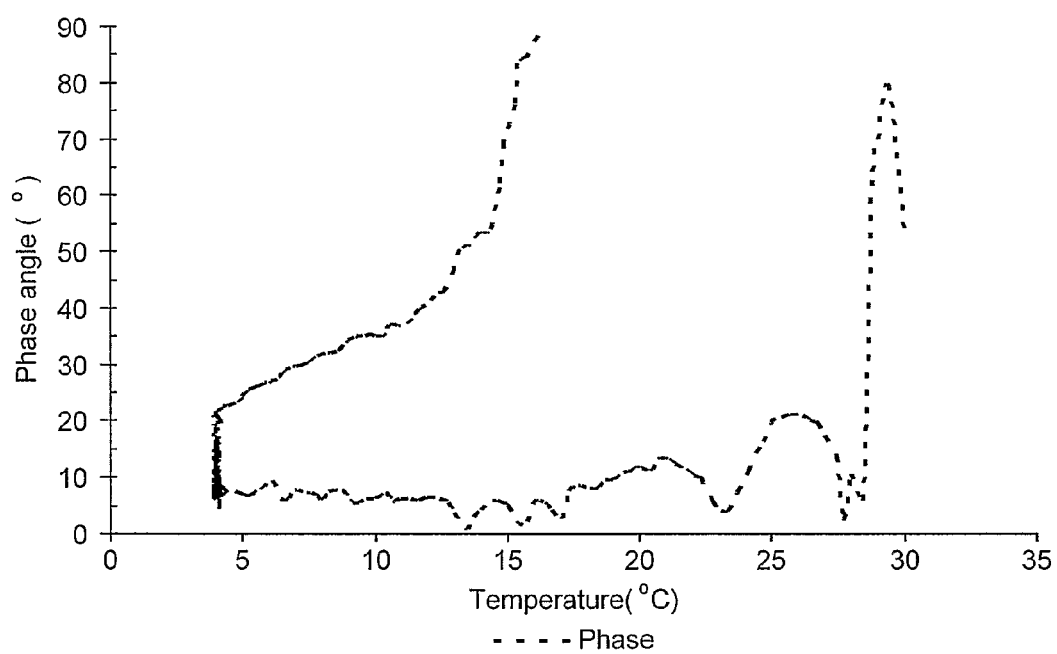
Figure 4C:
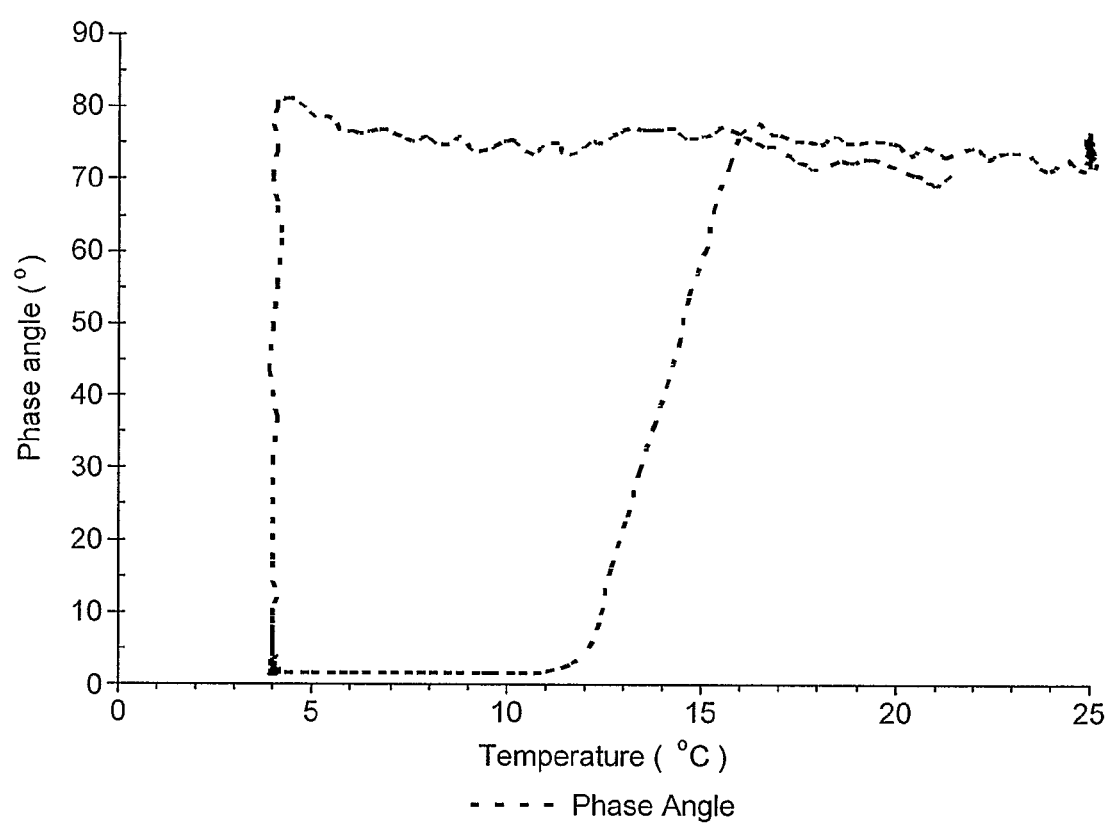

Gelling and Melting Temperatures of an Aqueous Blend of Fish Gelatin and Kappa-Carrageenan FIG. 4a shows the gelling (Tg) and melting (Tm) temperatures of a blend of 0.5% kappa-carrageenan and 10% fish gelatin, whereas FIGS. 4b and 4c present the same values for the two single components (0.5% kappa-carrageenan (1b) and 10% fish gelatin (1c), respectively). These results are presented as a change in the phase angle at small oscillatory measurements (=arctan G"/G') reflecting the change from a predominantly solid to a predominantly fluid ($\delta$=450) system and vice versa.

It is clearly seen that this mixture represents a true synergistic system in the sense that neither of the two components alone give a gel at room temperature, whereas the mixed system surprisingly gives gelling (~27° C.) and melting (~40° C.) temperatures close to those of mammalian gelatin gels.

EXAMPLE 5

Gel Strength Development of a Blend of Fish Gelatin and Kappa-Carrageenan

Figure 5A:
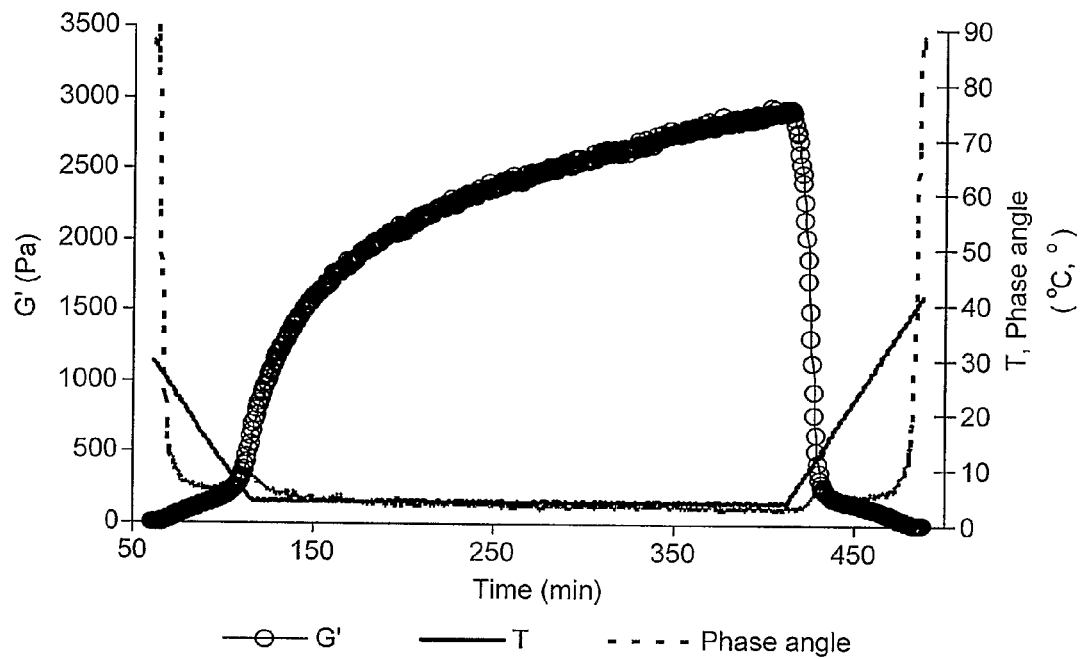
FIG. 5*a* (small-strain oscillatory measurements of 0.5 (w/v) % kappa-CG and 10 (w/v) % FG cooled to 4° C. Extrapolation to G'infinite gives G'=3620 Pa), 5*b* (results from small-strain oscillatory measurements of 0.5 (w/v) % κ-CG cooled to 40° C.; 5*c* (results from small-strain oscillatory measurements of 10 (w/v) % FG cooled to 4° C. Extrapolation to $G'_{infinite}$ gives G'=1100 Pa) are plots of temperature (T), elastic modulus (G') and phase angle (δ) for three compositions which are cooled from 20 to 4° C. and then heated up to 40° C.
Figure 5B:
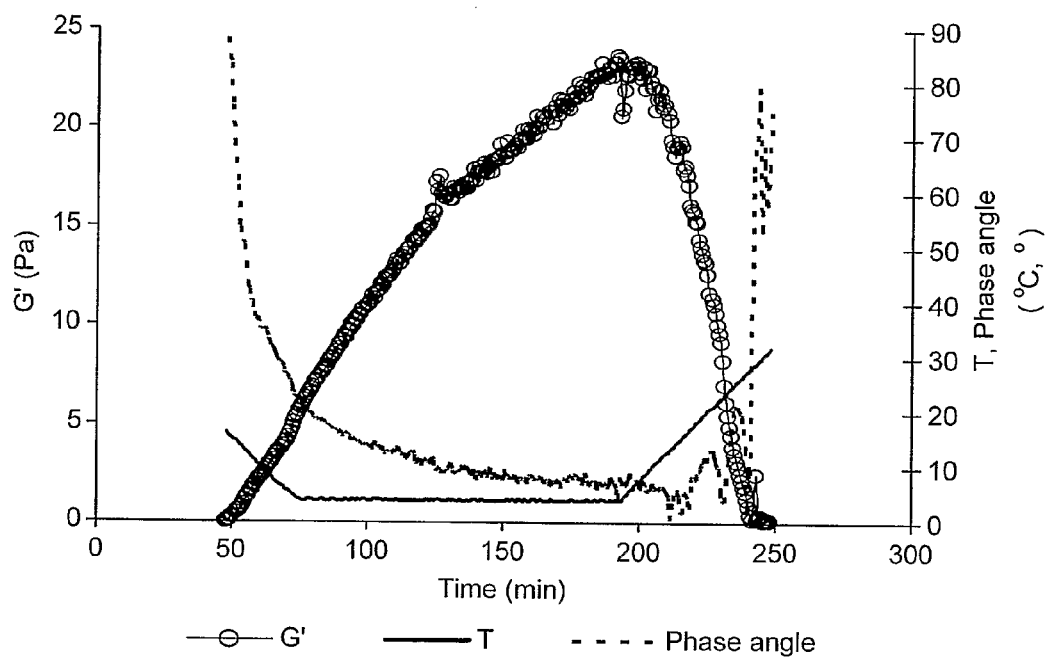
Figure 5C:
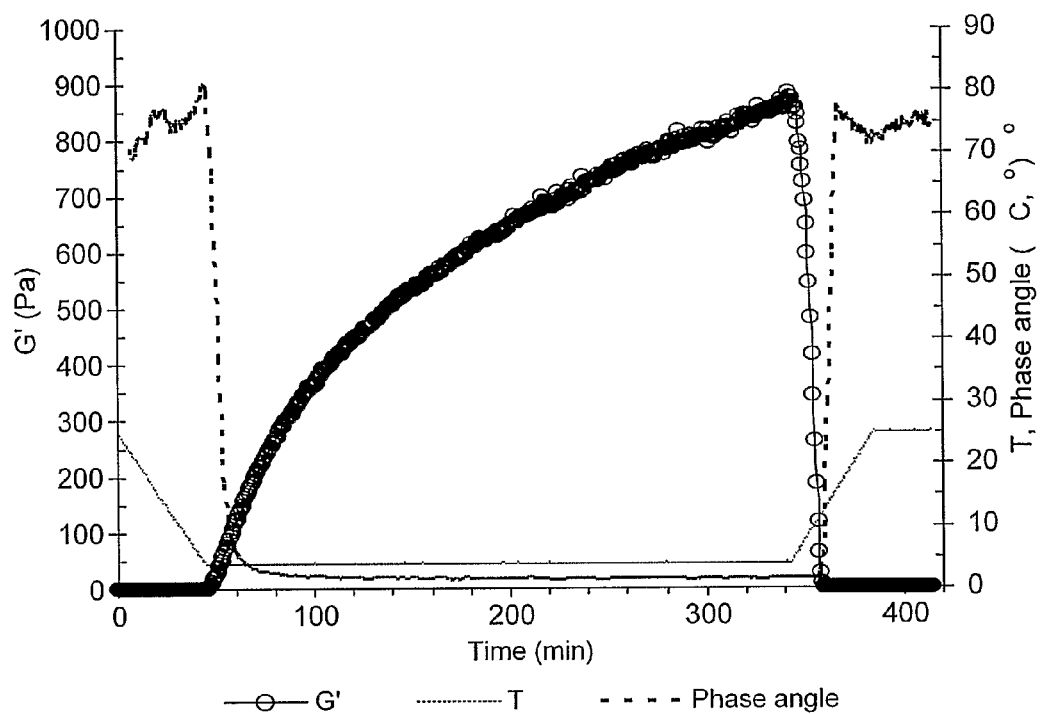

FIG. 5a presents the development in gel strength (given as the dynamic storage modulus (G') from small strain oscillatory measurements) of a mixture of 0.5% kappa-carrageenan and 10% fish gelatin. The corresponding development of the two components alone (0.5% kappa-carrageenan and 10% fish gelatin) are given in FIGS. 5b and 5c, respectively. All results are obtained at 4° C. since neither of the two components alone gives gels at room temperature (see also Example 1). From the present set of data, it is again obvious that a true synergistic system is obtained since G' of the mixed system is substantially higher than the G' values measured for the two components alone.

EXAMPLE 6

Strength of Mixed Fish Gelatin/Kappa-Carrageenan Gels at High FG Concentration

Figure 6:
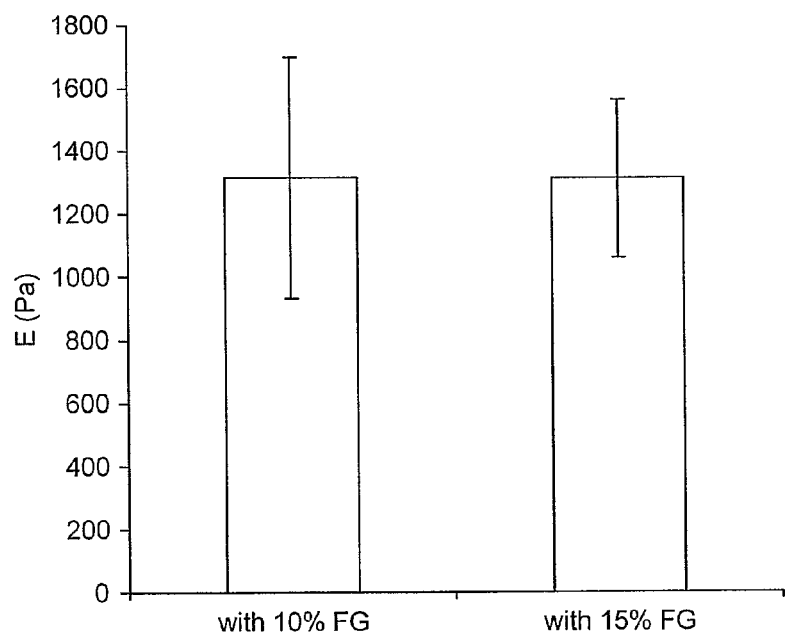
FIG. 6 is a graph showing Young's modulus (E) for mixed systems of 0.5 (w/v) % κ-CG and 10 or 15 (w/v) % FG at room temperature (average±S.D, n>4)

FIG. 6 shows the gel strength (given as Young's modulus (E) from compression analysis) of 0.50% kappa-carrageenan mixed with 10 and 15% fish gelatin without any salt added. Example 4 showed that neither of the two components alone gives stable gels at room temperature, but that a blend of 0.50% kappa-carrageenan and 10% fish gelatin does. FIG. 6 shows that this result also is valid at a 15% inclusion of fish gelatin. In fact, there is no significant effect on gel strength in this mixed system going from a 1:20 to a 1:30 ratio between kappa-carrageenan and fish gelatin, a result which proves the robustness of this mixed system.

EXAMPLE 7

Fish gelatin with an average molecular weight of 55000 Da is dissolved in PBS to 5% wt. and 500 µL added to 8 tissue inserts. The membrane in the tissue inserts is covered with an epidermis model, 17 days old, from SkinEthic, France.

1 mL of PBS is added to wells in a 24-well plate. One tissue insert with fish gelatin solution is put into 8 wells in the multi-well plate. The system is incubated at 30° C. and one tissue insert removed every 30 minutes for 3 hours and every hour until 5 hours. The solutions in the wells are collected and the absorbance at 280 nm measured to indicate that fish gelatin molecules have penetrated the epidermis models. Increasing absorbance values with time indicate that fish gelatin molecules penetrate the epidermis model on incubation at 30° C.

EXAMPLE 8

Fish gelatin with an average molecular weight of 120000 Da is dissolved in PBS to 5% wt. A low molecular weight fraction of fish gelatin with an average molecular weight of 30000 Da is added to a concentration of 2.5% wt. 500 μL of the fish gelatin solution is added to 8 tissue inserts. The membrane in the tissue inserts is covered with an epidermis model, 17 days old, from SkinEthic, France.

1 mL of PBS is added to wells in a 24-well plate. One tissue insert with fish gelatin solution is put into 8 wells in the multi-well plate. The system is incubated at 30° C. and one tissue insert removed every 30 minutes for 3 hours and every hour until 5 hours. The solutions in the wells are collected and the absorbance at 280 nm measured to indicate that fish gelatin molecules have penetrated the epidermis models. Increasing absorbance values with thim indicate that fish gelatin molecules penetrate the epidermis model on incubation at 30° C.

EXAMPLE 9

Fish gelatin with an average molecular weight of 30000 Da was dissolved in PBS to 5% wt. and 500 μL was added to 16 tissue inserts. The membrane in the tissue inserts was covered with an epidermis model, 20 days old, from SkinEthic, Nice, France (lot no.: 06022A 0304).

700 μL of PBS was added to wells in a 24-well plate. One tissue insert with fish gelatin solution was put into 16 wells in the multi-well plate. The system was incubated at 30° C. with gentle shaking and one tissue insert was removed every 20 minutes for 3 hours and every 30 minutes until 6.5 hours. The solutions in the wells and the inserts were collected and the absorbance at 280 nm measured both below and above the epidermis model to indicate that fish gelatin molecules have penetrated the barrier. Increasing absorbance values with time in the solution below the barrier indicate that fish gelatin molecules penetrate the epidermis model on incubation at 30° C.

Figure 7:
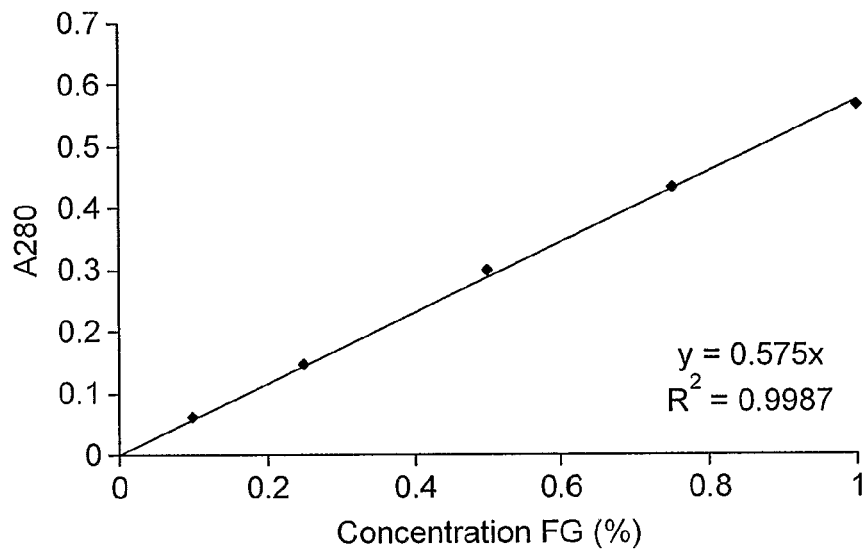
FIG. 7 is a plot of fish gelatin concentration against absorbance at 280 nm.

FIG. 7 shows the standard curve for the coherence between fish gelatin (average Mw=30000 Da) concentration in PBS and A280-values.

Table 4 below shows the absorbance values at 280 nm and the calculated fish gelatin concentrations in the PBS (700 μL) below the epidermis model inserts. PBS was used as the blank sample. The standard curve showing the coherence between fish gelatin concentration and A280 was used to calculate the fish gelatin concentrations as function of time.

TABLE 1

| Time (min) | A280 | Concentration of FG in PBS below barrier (%) |
|---|---|---|
| 0 | 0.000 | 0.00 |
| 20 | 0.0316 | 0.05 |
| 40 | 0.0366 | 0.06 |
| 60 | 0.0391 | 0.07 |
| 80 | 0.0507 | 0.09 |
| 100 | 0.0583 | 0.10 |
| 120 | 0.0626 | 0.11 |
| 140 | 0.0859 | 0.15 |
| 160 | 0.1064 | 0.19 |
| 180 | 0.0849 | 0.15 |
| 210 | 0.1022 | 0.18 |
| 240 | 0.1077 | 0.19 |
| 270 | 0.1174 | 0.20 |
| 300 | 0.1379 | 0.24 |
| 330 | 0.1599 | 0.28 |
| 360 | 0.1837 | 0.32 |
| 390 | 0.2166 | 0.38 |

Figure 8:
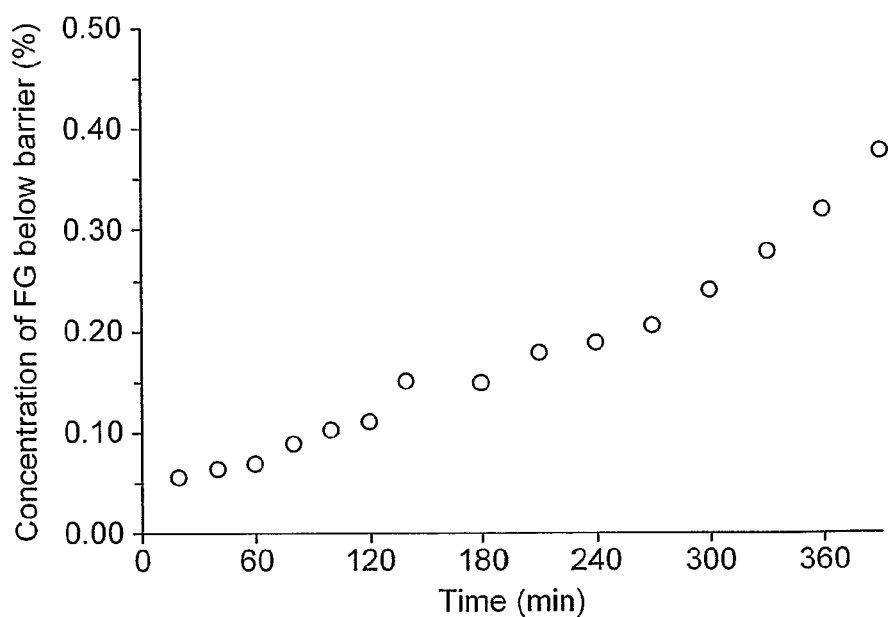
FIG. 8 is a plot of fish gelatin concentration against time.

The data of Table 1 is plotted in FIG. 8 as concentration of FG in PBS below barrier as a function of time.

The maximum possible concentration of FG at equilibrium in the system is calculated to be about 2.08%. This means that 19% of the FG has penetrated the epidermis barrier at 6.5 hours.

The invention claimed is:

1. A topical pharmaceutical or cosmetic composition comprising a pharmaceutically or cosmetically active agent and a gelling agent, wherein said gelling agent comprises a fish gelatin and a polysaccharide, wherein said fish gelatin has a weight average molecular weight in the range 90-140 kDa, wherein said polysaccharide is kappa-carrageenan having a weight average molecular weight of 400 to 800 kDa, wherein said composition has a continuous aqueous phase having a melting temperature in the range 20 to 42° C., wherein said polysaccharide is present at a concentration of 0.5-0.75% wt, and wherein said fish gelatin is present at a concentration of 10 to 15% wt.

2. The composition of claim 1 containing a continuous aqueous phase having a gelling temperature in the range 10 to 30° C.

3. The composition of claim 2 wherein the gelling temperature is in the range 15 to 28° C.

4. The composition of claim 1, wherein the melting temperature is in the range 24 to 40° C.

5. The composition of claim 4 wherein the melting temperature is in the range 28 to 37° C.

6. The composition of claim 1 wherein the fish gelatin has an imino acid content of 5 to 25% wt.

7. The composition of claim 1 wherein the pH of the composition is in the range 5 to 7.5.

8. The composition of claim 1 containing a pharmaceutically active agent selected from the group consisting of antibiotics, antiinflammatories, antipruritics, steroids, NSAIDs, antifungals and anti-acne compounds.

9. The composition of claim 1 containing as a cosmetically active agent a skin hydrating agent.

10. A method of treatment of a human subject comprising applying to the skin of said subject an effective amount of a pharmaceutical composition according to claim 1.

11. A method of cosmetic treatment of a human subject comprising applying to the skin thereof a cosmetic composition according to claim 1.

12. A process for the manufacture of a composition according to claim 1, which process comprises admixing said fish gelatin, said polysaccharide, and said pharmaceutically or cosmetically active agent.

* * * * *